United States Patent
Dale et al.

[11] Patent Number: 6,106,888
[45] Date of Patent: Aug. 22, 2000

[54] PROCESS FOR TREATING CELLULOSIC MATERIALS

[75] Inventors: Bruce E. Dale, Mason; Justin K. Weaver, Charlotte, both of Mich.

[73] Assignee: Board of Trustees operating Michigan State University, East Lansing, Mich.

[21] Appl. No.: 09/232,980

[22] Filed: Jan. 19, 1999

Related U.S. Application Data

[62] Division of application No. 09/070,576, Apr. 30, 1998.

[51] Int. Cl.[7] .................. A23K 3/00; A23P 1/14
[52] U.S. Cl. .................. 426/636; 426/516; 426/519; 426/520; 426/807
[58] Field of Search .................. 426/635, 636, 426/506, 516, 519, 520, 807

[56] References Cited

U.S. PATENT DOCUMENTS

| | | |
|---|---|---|
| 4,356,196 | 10/1982 | Hultquist . |
| 4,559,376 | 12/1985 | Kubat et al. .................. 524/13 |
| 4,600,590 | 7/1986 | Dale . |
| 4,644,060 | 2/1987 | Chou . |
| 5,037,663 | 8/1991 | Dale . |
| 5,171,592 | 12/1992 | Holzapple . |
| 5,192,543 | 3/1993 | Irvin et al. .................. 425/378.1 |
| 5,473,061 | 12/1995 | Bredereck et al. .................. 536/59 |
| 5,498,766 | 3/1996 | Stuart et al. .................. 435/99 |
| 5,772,721 | 6/1998 | Kazemzadeh .................. 71/11 |

FOREIGN PATENT DOCUMENTS 0 077 287  6/1988  European Pat. Off. .

OTHER PUBLICATIONS

Dale, B. E., et al., Biotechnology and Bioengineering Symp. No. 12, 31–34 (1982).
Dale, B. E., et al., Developments in Industrial Microbiology, A Publication of the Society for Industrial Microbiology, vol. 26 (1985).
Holtzapple, M.T., et al., Applied Biochemistry and BioTechnology vol. 28/29, 59–74 (1991).
Blasig, J.D., et al., Resources, Conservation and Recycling, 7:95–114 (1992).
Reshamwala, S., et al., Applied Biochemistry and BioTechnology vol. 51/52, 43–55 (1995).
Dale, B.E., et al., Bioresource Technology 56:111–116 (1996).
Moniruzzaman, M., et al., Applied Biochemistry and Biotechnology, 67:113–126 (1997).

*Primary Examiner*—Keith D. Hendricks
*Assistant Examiner*—Drew Becker
*Attorney, Agent, or Firm*—Ian C. McLeod

[57] ABSTRACT

A process and screw in barrel apparatus (10) for expanding cellulosic materials is described. The expanded cellulosic material is useful as an animal feed and a nutrient source for fermentation processes.

6 Claims, 12 Drawing Sheets

PROCESS FOR TREATING CELLULOSIC MATERIALS

This is a divisional of copending U.S. Patent application No. 09/070,576 filed Apr. 30, 1998.

BACKGROUND OF THE INVENTION

The present invention relates to the use of a process and apparatus with a screw in a barrel for treating cellulosic materials in order to expand the materials, thereby making them more useful as animal feeds and for fermentation processes, for instance. In particular the present invention relates to a screw in a barrel process and apparatus which provides continuous processing of the cellulosic material using liquid ammonia which expands the cellulosic material while changing from a liquid to a gas upon exiting the apparatus.

DESCRIPTION OF RELATED ART

The use of ammonia under pressure to increase protein availability and cellulosic digestibility of a cellulosic containing plant material (alfalfa) is described in U.S. Pat. No. 4,356,196 to Hultquist. The ammonia which is provided in a vessel in liquid form impregnates the plant material and is explosively released upon being exposed to a rapid reduction in pressure in the vessel. The resulting processed material is used for ethanol production or as a feedstock for food or dairy animals. Dale in U.S. Pat. Nos. 4,600,590 and 5,037,663 describes the use of various volatile chemical agents to treat the cellulose containing materials, particularly ammonia, by what came to be known as the AFEX process (Ammonia Freeze or Ammonia Fiber Explosion). The process pressures were somewhat higher than in Hultquist. Holzapple et al in U.S. Pat. No. 5,171,592 describe an improved AFEX process wherein the treated biomass product is post-treated with super heated vapors of a swelling agent to strip the residual swelling agent for recycling. The apparatus 20 has mixing and a staged valve 21 which periodically opens. U.S. Pat. No. 4,644,060 to Chou is of general interest in use of supercritical ammonia to liberate polysaccharides. The patented processes are essentially accomplished on a batch basis.

Other prior art references relating to the AFEX process are European Patent No. 0 077 287; Dale, B. E., et al., Biotechnology and Bioengineering Symp. No. 12, 31–43 (1982); Dale, B. E., et al., Developments in Industrial Microbiology, A Publication of the Society for Industrial Microbiology, Vol. 26 (1985); Holtzapple, M. T., et al., Applied Biochemistry and Biotechnology Vol. 28/29, 59–74 (1991); Blasig, J. D., et al., Resources, Conservation and Recycling, 7:95–114 (1992); Reshamwala, S., et al., Applied Biochemistry and Biotechnology Vol. 51/52, 43–55 (1995); Dale, B. E., et al., Bioresource Technology 56:111–116 (1996); and Moniruzzaman, M., et al., Applied Biochemistry and Biotechnology, 67:113–126 (1997). Each of these processes are non-continuous.

OBJECTS

It is therefore an object of the present invention to provide an improved continuous process for producing an expanded cellulosic material using a swelling agent. It is further an object of the present invention to provide a novel apparatus which is particularly adapted for practicing the process. These and other objects will become increasingly apparent by reference to the following description and the drawings.

DESCRIPTION OF PREFERRED EMBODIMENTS

The present invention relates to an improvement in a process for expanding a cellulosic material by contacting the cellulosic material with a swelling agent which impregnates the cellulosic material and then rapidly reducing the pressure to thereby expand the cellulosic material by gaseous expansion of the swelling agent, which comprises: (a) injecting the swelling agent and the cellulosic material into a screw in a barrel having a feed throat leading to the screw in rotating contact with the barrel along part of a length of the screw so that the screw is sealed in operation, with an inlet for feeding the swelling agent into the feed throat under pressure to the screw and with an outlet from the barrel adjacent to the screw; (b) compacting the swelling agent and cellulosic material by rotation of the screw in the barrel; (c) removing the swelling agent and the cellulosic material from the barrel through the outlet from the extruder so that the swelling agent expands the cellulosic material; and (d) optionally recovering the swelling agent from the cellulosic material.

Further the present invention relates to an improved apparatus with at least one rotatable screw mounted in a barrel with opposed ends, a feed inlet to the screw through the barrel, and a feed outlet from the screw and removal through the barrel, and optional heating and cooling means between the ends of the barrel, which comprises: a liquid inlet to the screw through the barrel intermediate the ends, whereby the liquid is fed to the screw under pressure so that a cellulosic material is expanded or by change of the liquid to a gas upon removal of the cellulosic material from the barrel by the rotation of the screw.

The present invention also relates to a system for expanding a cellulosic material which comprises: (a) an apparatus with at least one rotatable screw mounted in a barrel with opposed ends, a feed inlet to the screw through the barrel, and a feed outlet from the screw and removal through the barrel, and optional heating and cooling means between the ends of the barrel, which comprises a liquid inlet to the screw through the barrel intermediate the ends, whereby the liquid is fed to the screw under pressure so that a cellulosic material is expanded upon removal of the cellulosic material from the barrel by the liquid becoming a gas by the rotation of the screw; (b) a liquid supply under pressure to the inlet of the liquid inlet; (c) a confined space in which the system is placed; and (d) gas removal means adjacent the ends of the barrel for removing gas which is released upon expansion of the material.

The primary goal of this invention is in the use of a screw and barrel apparatus 10 (shown in FIG. 1) to improve the Ammonia Fiber Explosion (AFEX) Process, which had previously performed only in a batch reactor. Effectiveness of the treatment using the extruder apparatus 10 was defined as an increase in enzymatic or rumen in situ digestibility.

EXAMPLE 1

Figure 1:
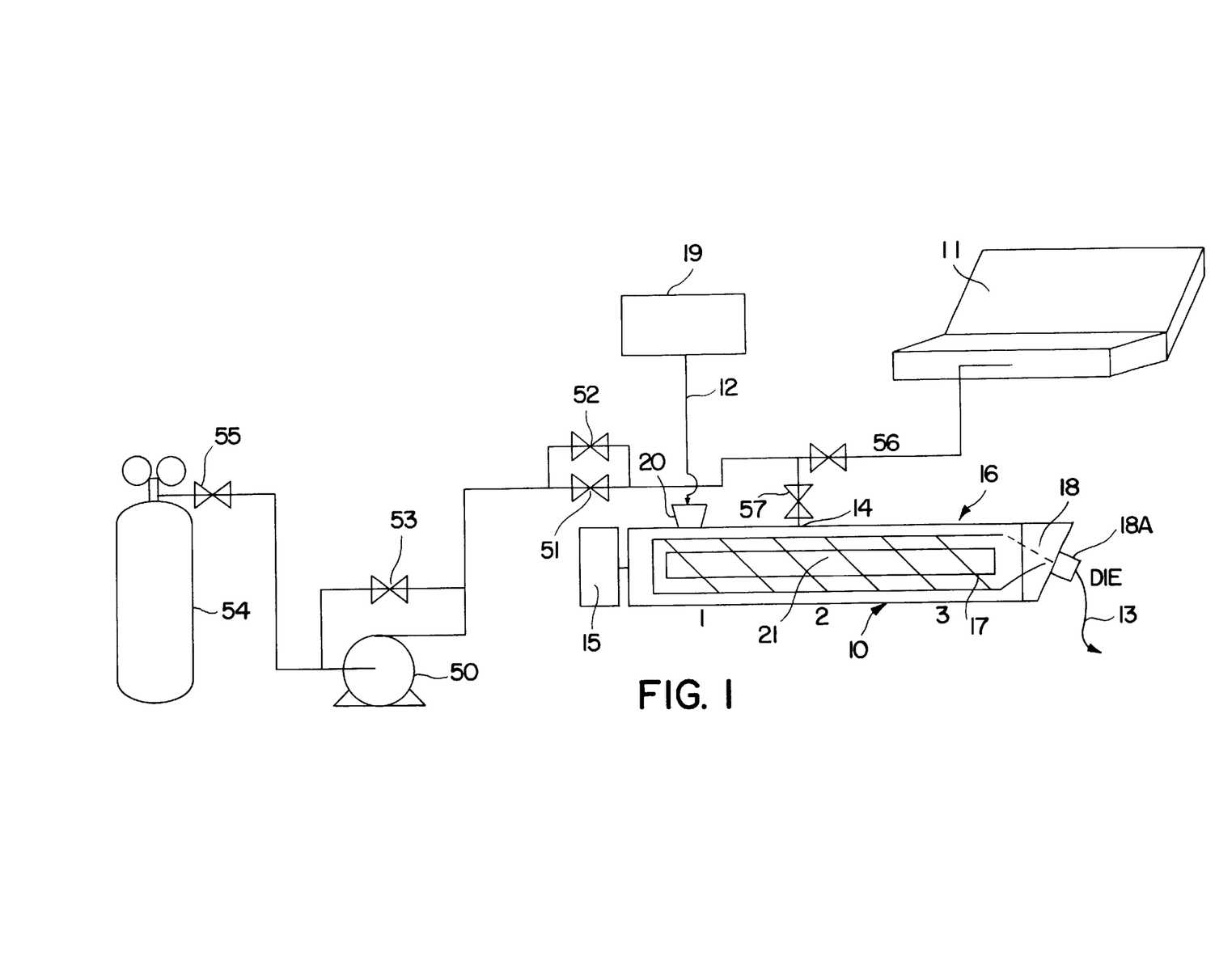
FIG. 1 is a schematic drawing showing a screw apparatus 10 for the process.
Figure 2:
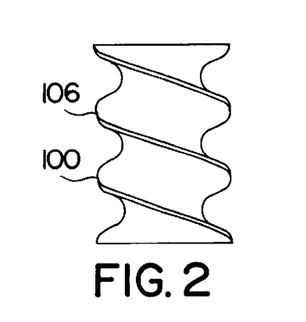
FIG. 2 is a side view of an individual screw element 100 showing individual flights 106.
Figure 3:
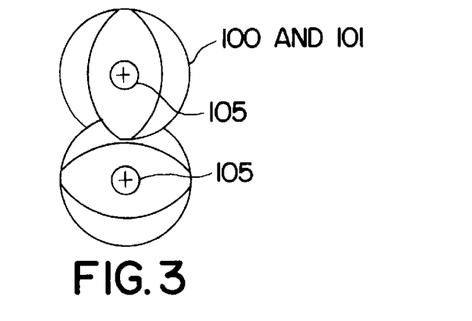
FIG. 3 is an end view of two (2) of the screw elements 100 and 101 acting together along parts of parallel dual shafts 21.
Figure 4:
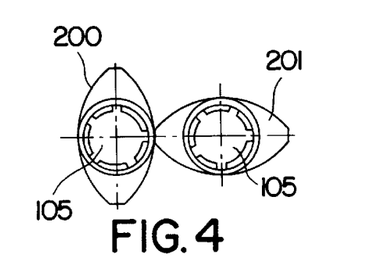
FIGS. 4 and 5 are end cross-sectional views of kneading blocks 200 and 201 in various positions relative to each other which are acting in parallel along parts of dual shafts 21.
Figure 5:
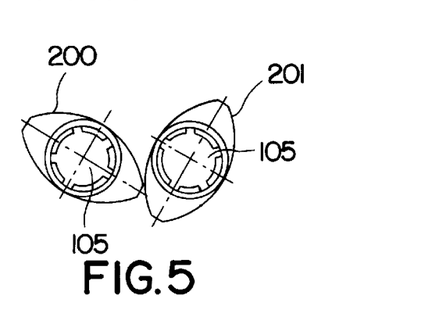
Figure 6A:
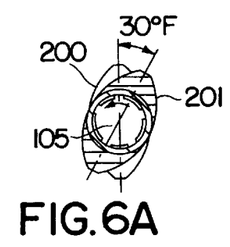
FIGS. 6A to 6I are end cross-sectional views of kneading blocks 200 and 201 of FIGS. 4 and 5 in various relative positions.
Figure 6B:
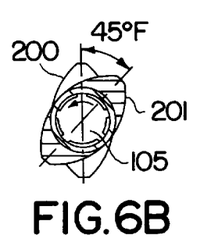
Figure 6C:
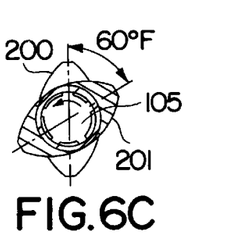
Figure 6D:
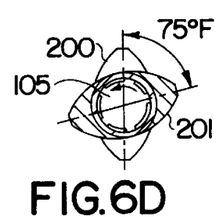
Figure 6E:
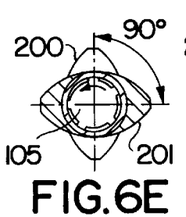
Figure 6F:
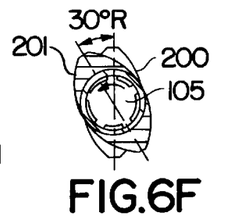
Figure 6G:
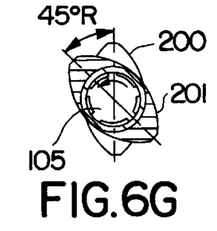
Figure 6H:
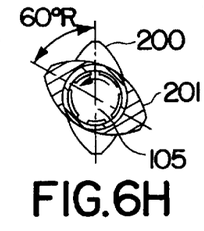
Figure 6I:
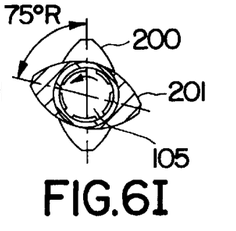
Figure 7:
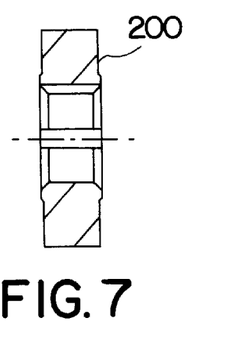
FIGS. 7 and 8 show cross-sectional and end views of an individual kneading block 200.
Figure 8:
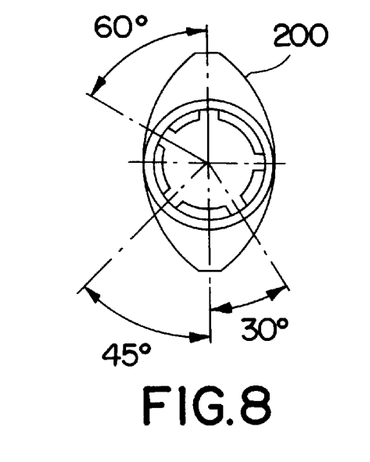
Figure 9:
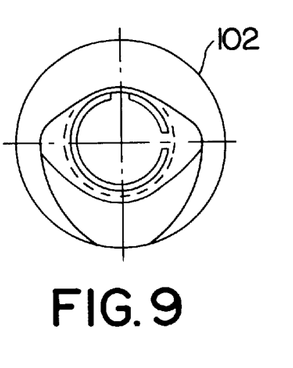
FIG. 9 is an end view of a camel screw element 102 which is adjacent to an extrusion die 18 from the apparatus and which forces the cellulosic material into the die block 18 and through die 18A.
Figure 10:
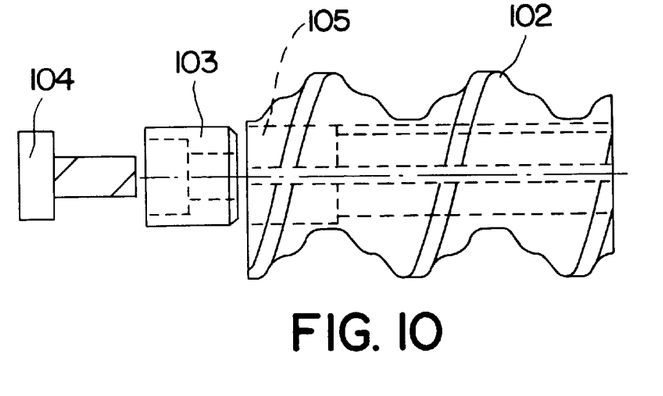
FIG. 10 is a side view of the camel back screw element 102 of FIG. 9 which also shows a plug 103 and screw 104 for holding screw element 102 on a rod 105 (which acts as shaft 21 of FIG. 1) supporting the screw elements 100 and 101 and the kneading blocks 200 and 201 along the screw 17.

The first step was to develop a safe environment in which to work with ammonia. To do this, the Office of Radiation, Chemical, and Biological Safety (ORCBS) at Michigan State University (MSU), East Lansing, Michigan was contacted. Following their advice, the area around the extruder apparatus 10, which enclosed the supplemental ventilation units in the room, was completely surrounded with vinyl stripping to contain any ammonia leaks. Testing of this enclosure was done with a smoke bomb that emitted 10,000 $ft^3$ of smoke in 1 minute, none of which was observed to escape. Additionally, a horizontal fume hood 11 was attached to one of the ventilation ducts to concentrate ventilation immediately around the extruder feed 12 and outlet 13, as well as the ammonia injection port 14. Finally, two full-face respirators with removable ammonia cartridges were purchased for use during all experimentation. A safety protocol was developed and reviewed with each person assisting in any experimentation.

Figure 11:
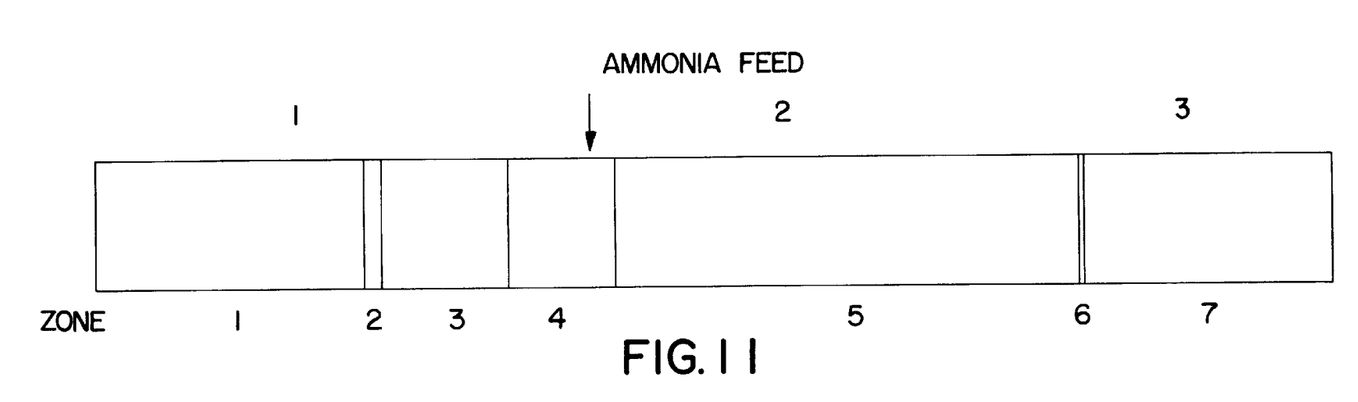
FIG. 11 is a side schematic view of an extrusion screw showing various screw elements 100 and 101 and kneading blocks 200 and 201 in zones 1 to 7 as set forth in Table 1 hereinafter.

The extruder apparatus 10 was a Baker-Perkins MPC/V-30 (Saginaw, Mich.) with parallel twin screws 17 side by side, each made up of screw elements 100, 101 and 102 and kneading blocks 200 and 201 (FIGS. 2 to 10). The motor 15 supplied 3 HP at 500 RPM. The barrel 16 configuration diameter was 30 mm with a length to diameter ratio (L/D) of 10:1. The two (2) screws 17 were co-rotating and self wiping with a variable profile. FIG. 11 shows the position of the segments 100, 101, and 103 and kneading blocks 200 and 201. Table 1 shows the positions of the elements.

TABLE 1

| Zone | Element | Length |
|---|---|---|
| 1 | Forward Transport Screw | 3 13/16" |
| 2 | 1 Kneading Block | 1/4" |
| 3 | Forward Transport Screws | 1 3/4" |
| 4 | Mixing Zone 5 Kneading Blocks, 1/4", each, 5 total, 45° Alignment | 1 1/4" |
| 5 | Forward Transport Screw | 6 1/2" |
| 6 | Kneading Block | 1/8" |
| 7 | Modified Camel Back Discharge Screw | 3 1/2" |

The extruder apparatus 10 was supplied with controls (not shown) for both heating and cooling. Heating was supplied by electric cartridge heaters (+ in FIG. 12) in three zones along the barrel 16 and the die block 18. Cooling was supplied along the barrel 16 length by chilled water fed through cored barrel sections (ⓧ and O in FIG. 12). The dimensions are shown in Table 2.

Figure 12:
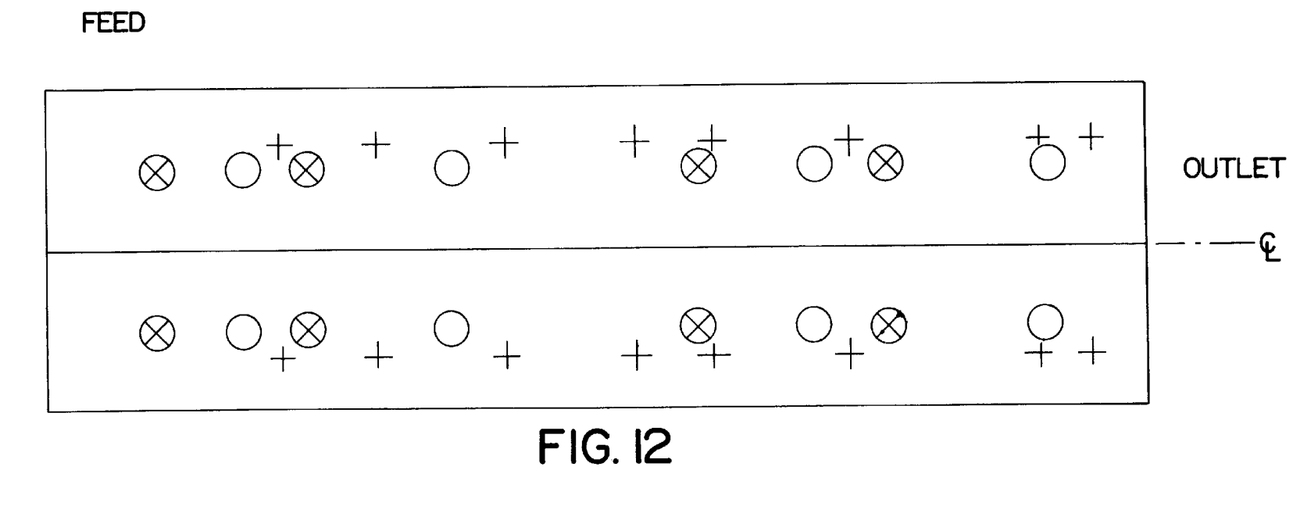
FIG. 12 is a side view of a heating and cooling block mounted along the longitudinal axis of the extruder apparatus 10 where $\widehat{x}$ is water outlet, O is water inlet and + is an electrical cartridge heater mounted in an opening in the barrel 16. Table 2 shows the dimensions for the various locations.

The barrel 16 and die block 18 are heated between about 30° C. to 100° C. along its length. Preferably the die block 18 is heated in this range.

TABLE 2

| Water Inlet Locations 1 1/8" above and below Centerline at: | Water Outlet Locations 1 1/8" above and below Center line at: | Heater Locations 1 1/2" above and below Centerline at: |
|---|---|---|
| 2 3/4" | 1/2" | 3 5/16" |
| 5 3/8" | 3 3/4" | 4 11/16" |
| 10 7/8" | 8 13/16" | 6 7/16" |
| 12 15/16" | 11 3/4" | 8 5/16" |
| | | 9 5/16" |
| | | 11 5/16" |
| | | 13 15/16" |
| | | 14 5/8" |

The die 18A through which the treated fodder was released, was air cooled. The die block 18 was provided with heaters (+ in FIG. 13). All interior surfaces of the extruder apparatus 10 were nitrided with a 63 μ-inch finish which provided excellent corrosion resistance. Screw elements 100, 101 and 102 and kneading block 200 and 201 (FIGS. 2, 3, 4, 5 and 6A to 6I) were made of heat treated alloy steel.

The corrosion resistance of a single screw element 100, 101 was determined prior to any experimentation and no corrosion was observed throughout the experimentation.

A reciprocating diaphragm metering pump 50 used to deliver ammonia was an American Lewa (Holliston, Mass.). The pump 50 head was made of 316 Stainless Steel with TEFLON seals. The pump 50 was capable of metering 0.23 to 23.0 GPH. The drive supplied 3 HP. The pump 50 was calibrated with water and the necessary conversions were done to determine the amount of liquid ammonia fed using a specified stroke length and speed setting.

All tubing, fittings, and valves used were of 316 SS. The tubing used was ⅜" OD with 0.065" walls, rated to 6500 psig. All fittings were rated to the burst pressure of the tubing. The pressure ratings of the materials used are well in the safe range. This was done to insure safety while working with ammonia. Most of the connections were Swagelok fittings, but a few were NPT. A check valve 51 and by-pass valves 52 and 53 were provided. An ammonia tank 54 with a shut-off valve 55 was the ammonia supply. A purge valve 56 was used to clear the system of ammonia. A needle valve 57 was used to meter ammonia into the extruder apparatus 10.

Biomass was fed into the extruder apparatus 10 via the feed tube 20. A feeder 19 to the feed tube 20 was calibrated by feeding material for a known period of time and determining the mass. Samples that contained different amounts of moisture were calibrated individually.

The primary material investigated in this project was corn fodder or stover. The sample material is also referred to herein as biomass. This includes all above ground portions of a corn plant except the grain and cob.

Corn fodder was obtained in a large square bale. This material was coarsely chopped using a tractor mounted grinder. The material was then dried (less than 5% moisture) and further milled to pass a 2 mm screen in a rotary knife mill. The size is between about 0.01 inch to 1 inch. The material was stored in plastic bags inside cardboard drums. Water was added in an amount by weight 10% to 80%. Fresh material can be used (usually at about 80% moisture, based upon dry matter weight).

The unmodified extruder apparatus 10 had been primarily used for processing of polymers and thus required significant modification. Thus, it was necessary to make several modifications. First, a port 14 was machined to allow the injection of ammonia. The port 14 was approximately half way down the length of the barrel 16. The port 14 was chosen to maximize the equilibration time of the biomass and ammonia. The equilibration time was approximately one (1) minute, but depended on feed rate, ammonia load, die temperature and the like. The injection port 14 was installed with a Teflon seal to minimize ammonia loss through the port 14.

Second, the screw 17 configuration was modified significantly in an effort to minimize ammonia loss through the feed tube 20. Additionally, two (2) camel screw elements 102 (one shown in FIGS. 9 and 10) were provided at the discharge end of the screw 17. originally these screws were flat on the end. The original design plugged the die block 18. By building the end of each of the screw 103 into a more conical shape, the biomass was directed into the die block 18 and out through the die 18A, rather than plugging.

The ammonia used was supplied in a 50 lb. cylinder 54 equipped with a dip tube to insure liquid delivery. The pump 50 allowed for control and accuracy in the delivery of ammonia. A check valve 51 was installed just prior to the injection port 14 to maintain the pressure on the ammonia in the tubing after the pump to help insure liquid delivery. Once the pressure generated by the pump 50 reached the cracking pressure of the check valve 51, the ammonia would flow directly into the extruder apparatus 10. The reseal pressure was set above the vapor pressure of ammonia to prevent any leakage through the check valve 51. Several bypass valves 52 and 53 were provided to allow the tubing to be purged by purge valve 56 after use of the extruder apparatus 10 to clean the apparatus.

Once it was verified that ammonia and biomass would flow together through the extruder apparatus 10, increasingly restrictive dies 18 were used. At first, the die block 18 was not used. However, as more confidence was gained, the block 18 was added, as well as die 18A. Several explosions were obtained with only the block 18 in use, but the enzymatic digestibility of the samples was only moderately higher than the untreated samples. Additionally, the increased pressure generated from a smaller orifice of the die 18A provided a more effective treatment.

Figure 13:
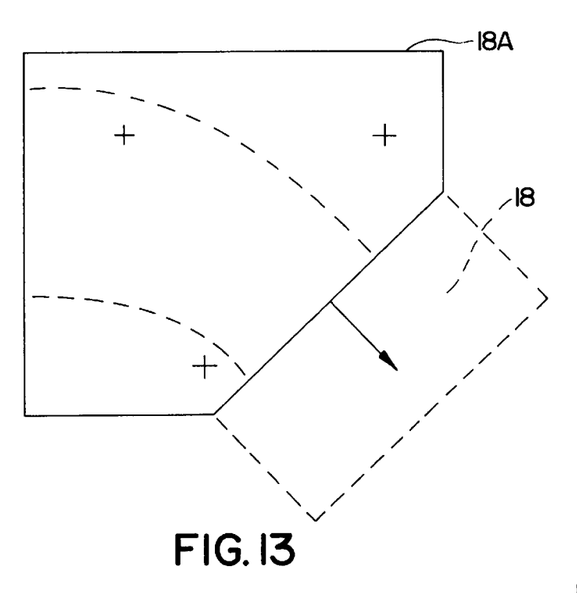
FIG. 13 is a side view of the die block 18.
Figure 14:
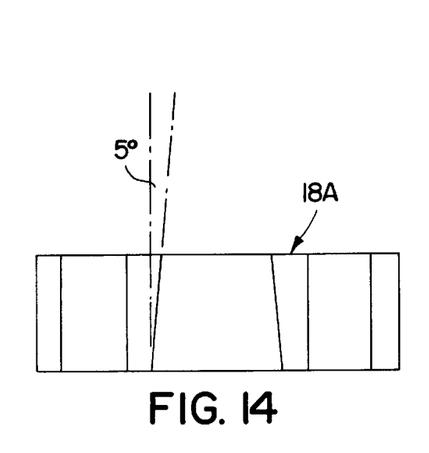
FIG. 14 is a top cross-sectional view of the die 18A.
Figure 15:
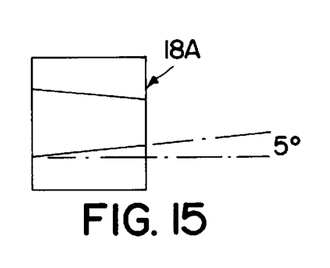
FIG. 15 is a side cross-sectional view of the die 18A.
Figure 16:
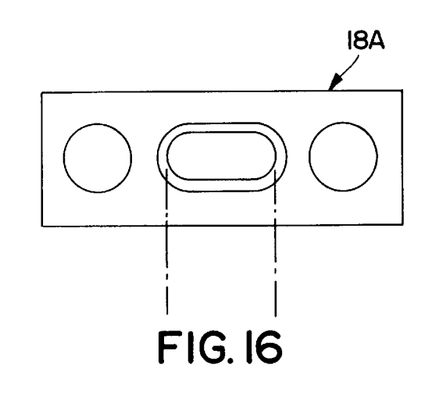
FIG. 16 is a view looking into the outlet from the die 18A.
Figure 17:
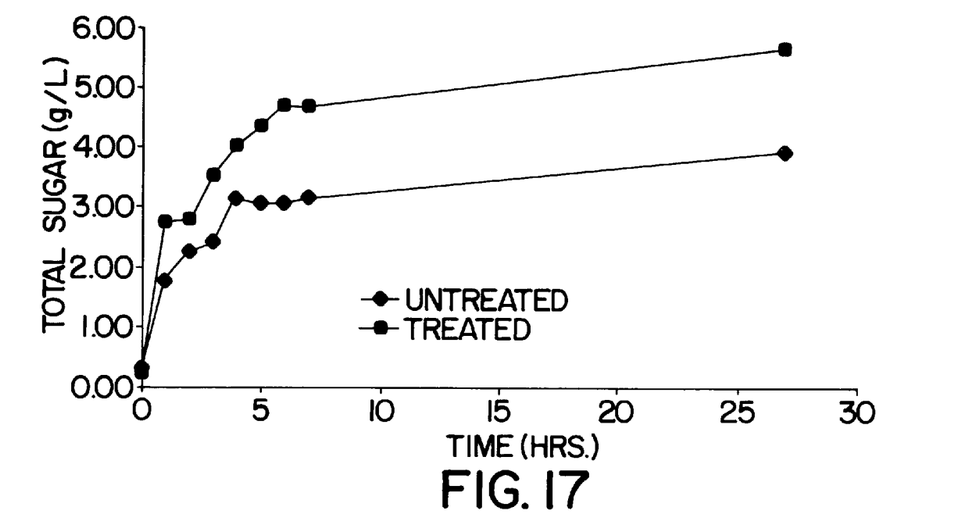
FIG. 17 is a graph showing total sugar concentration after enzymatic hydrolysis as a function of time for corn fodders which are treated by the process and apparatus of the present invention and those which are untreated. No die 18A or die block 18 was used. The extruder apparatus 10 was effective in increasing the total sugar concentration.

Much work has been done on the design of extrusion dies 18A. However, the biomass mixture is unlike any polymer or food which can be extruded throughout a standard die. Several preliminary dies 18A were tried with minimal success. These were machined by hand and the rough edges and interior surfaces created problems with biomass flow through the restriction. The die 18A that proved most useful was machined with a 5° end mill to give a smooth, gradual contraction of 40% of the inlet area (i.e., out let was 60% of the area of the inlet). With this die block 18, explosions could be consistently obtained. This die 18A is shown in FIGS. 13, 14 and 15. The dimensions are shown as follows:

Extrusion Die 18A

Larger Orifice is the inlet and faces the extruder.

$$\text{Area of larger Hole} = \left(\pi\left(\frac{0.5}{2}\right)\right)^2 + (1 - 0.5)0.5 = 0.446 \text{ in}^2$$

$$\text{Area of Smaller Hole} = (0.25 - y)[\pi(0.25 - y) + 1]$$

$$x = \frac{y}{\tan 5°}$$

Area of Smaller Orifice=0.268 in²

Figure 18:
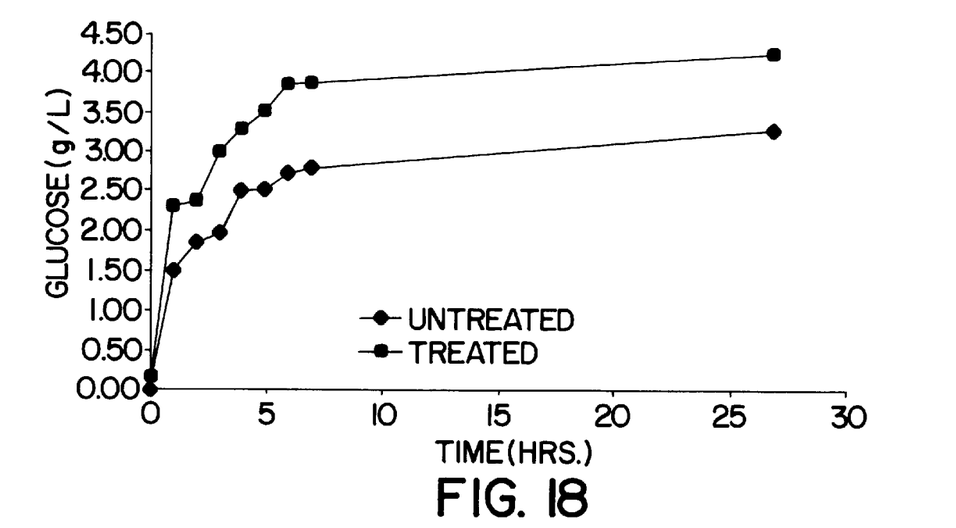
FIG. 18 is a graph showing glucose as a specific sugar treated in the same manner as in FIG. 17.
Figure 19:
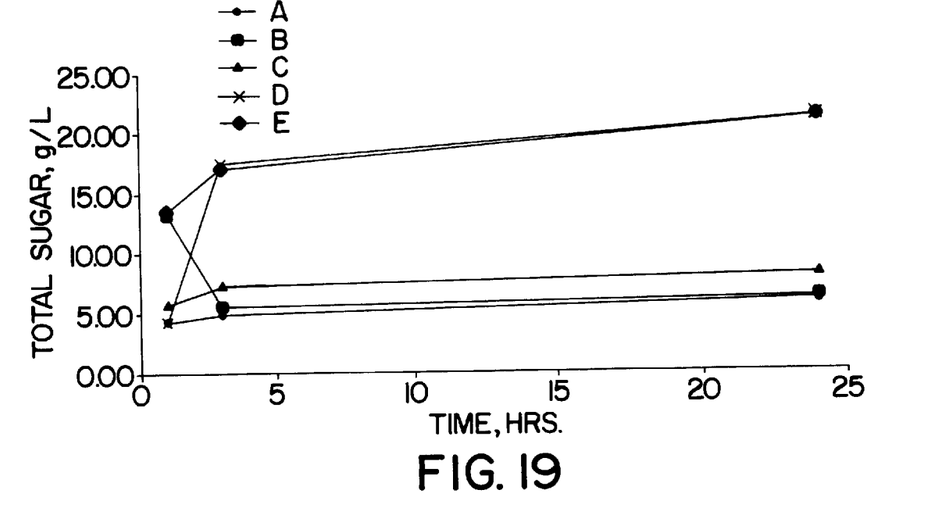
FIG. 19 is a graph showing total sugar concentration as a function of time for corn fodders treated by the process and apparatus of the present invention under different conditions.
Figure 20:
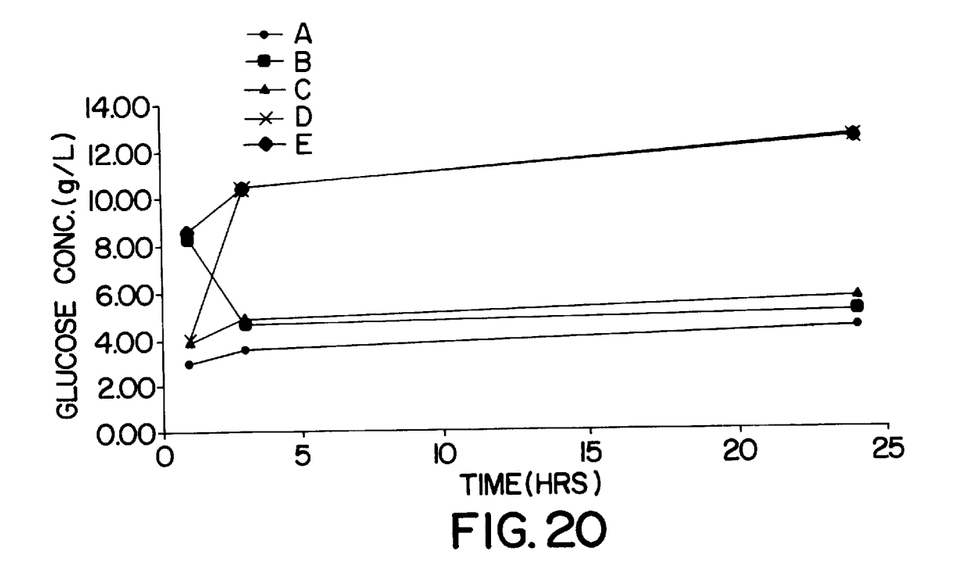
FIG. 20 is a graph showing glucose as a specific sugar treated in the same manner as in FIG. 19.
Figure 21:
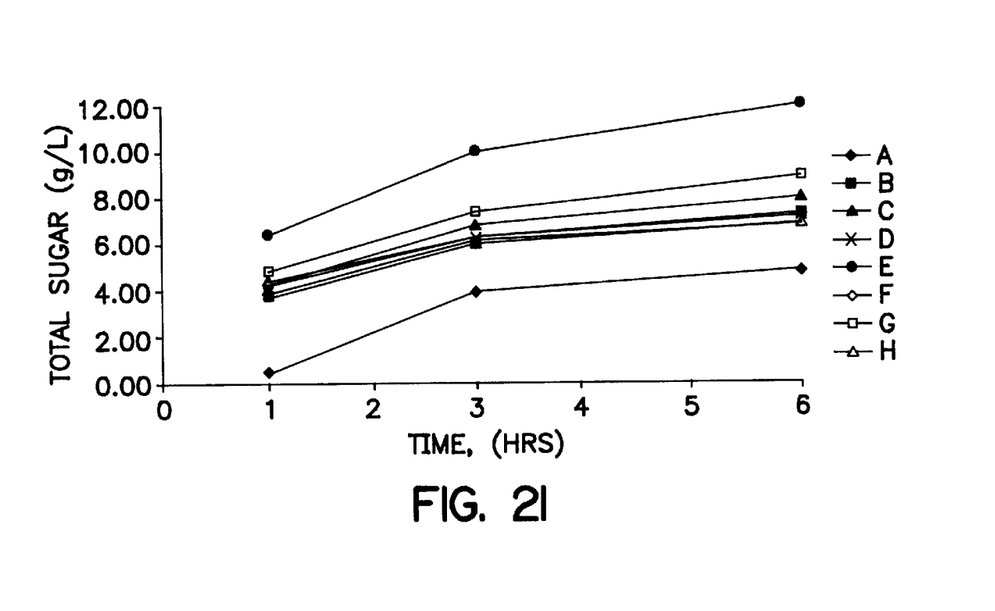
FIG. 21 is a graph showing total sugar concentration as a function of time for corn fodders treated by the process and apparatus of the present invention under different conditions.
Figure 22:
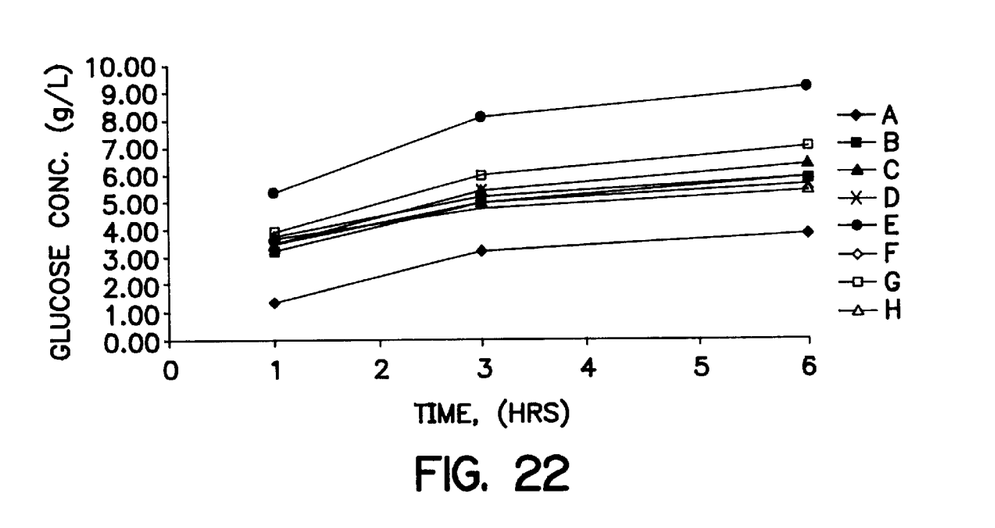
FIG. 22 is a graph showing glucose concentration as a specific sugar treated in the same manner as in FIG. 21.
Figure 23:
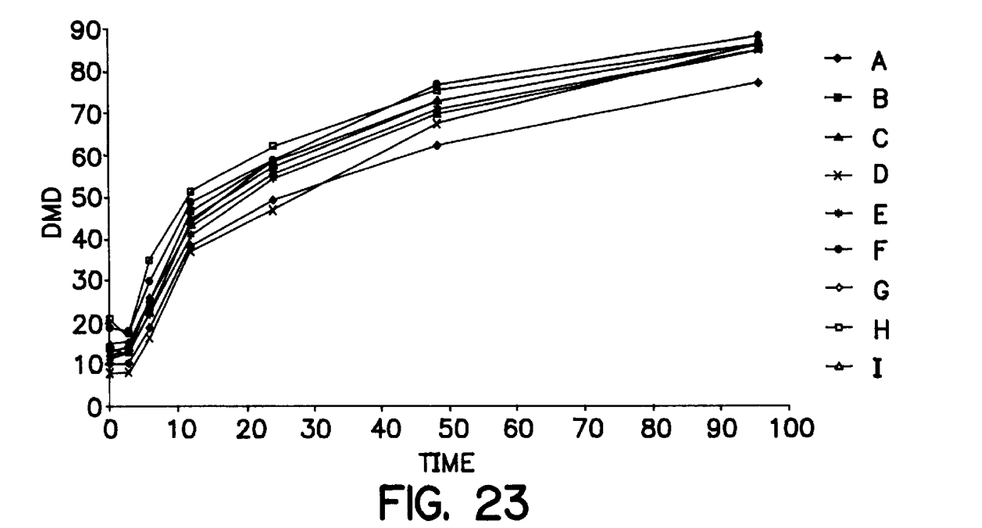
FIG. 23 is a graph showing in vivo digestibility of dry matter in corn fodder in the rumen of a cow as a function of time for various samples.
Figure 24:
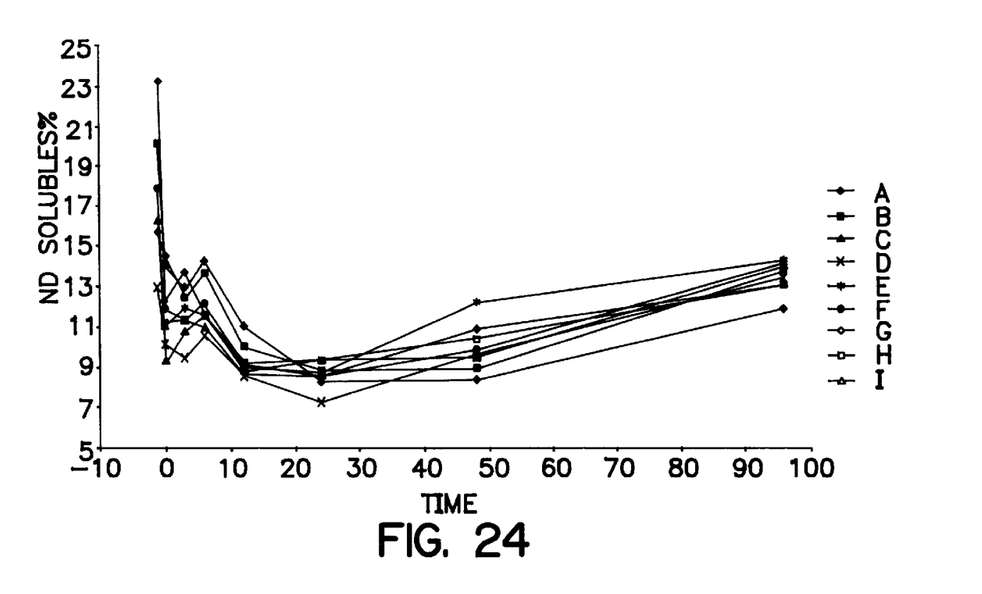
FIG. 24 is a graph showing NDF (Neutral Detergent Fibers) solubles concentration versus time for the samples of FIG. 23.
Figure 25:
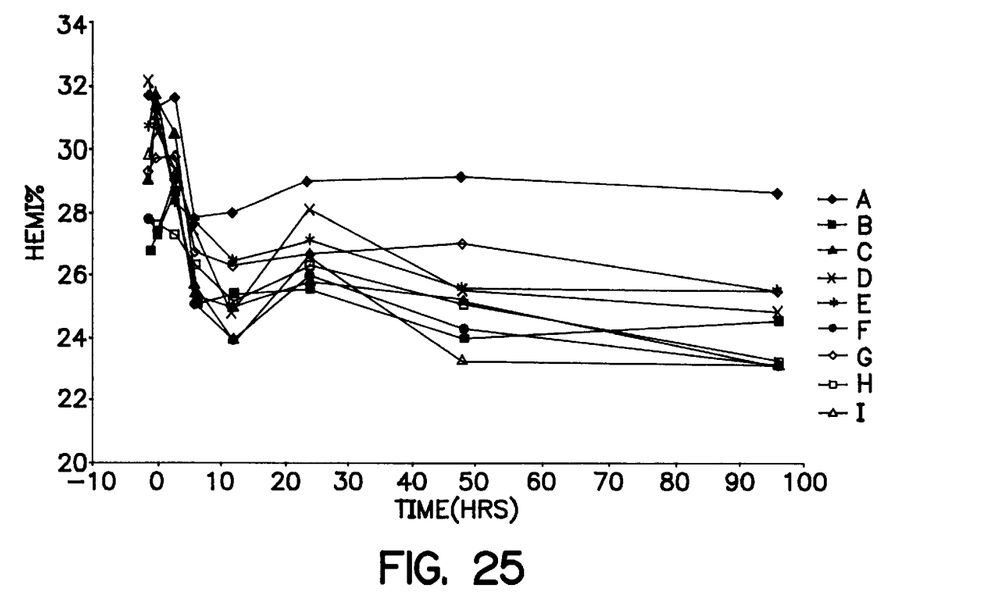
FIG. 25 is a graph showing hemicelluloses concentration versus time for the samples of FIG. 23.
Figure 26:
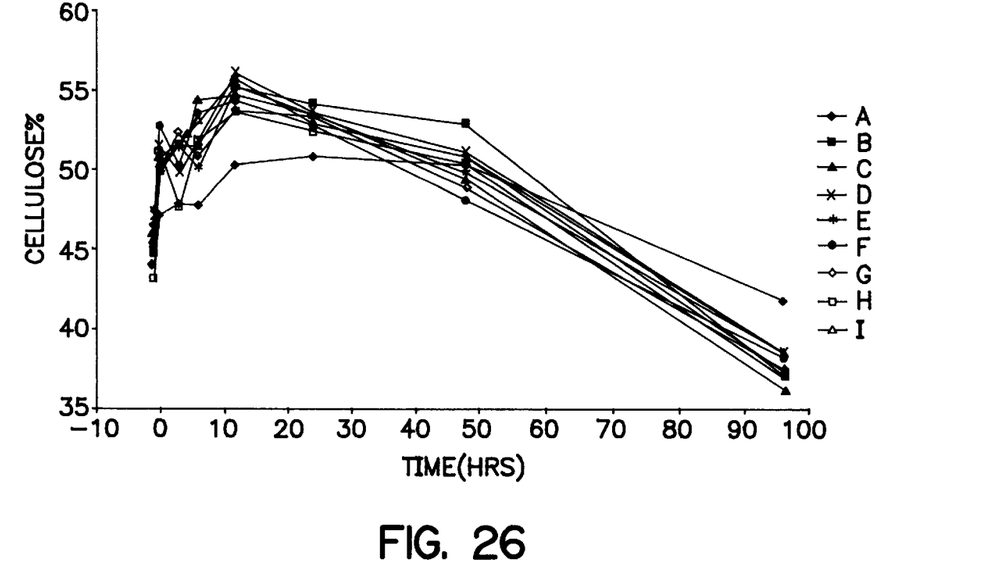
FIG. 26 is a graph showing cellulose concentration versus time for the samples of FIG. 23.
Figure 27:
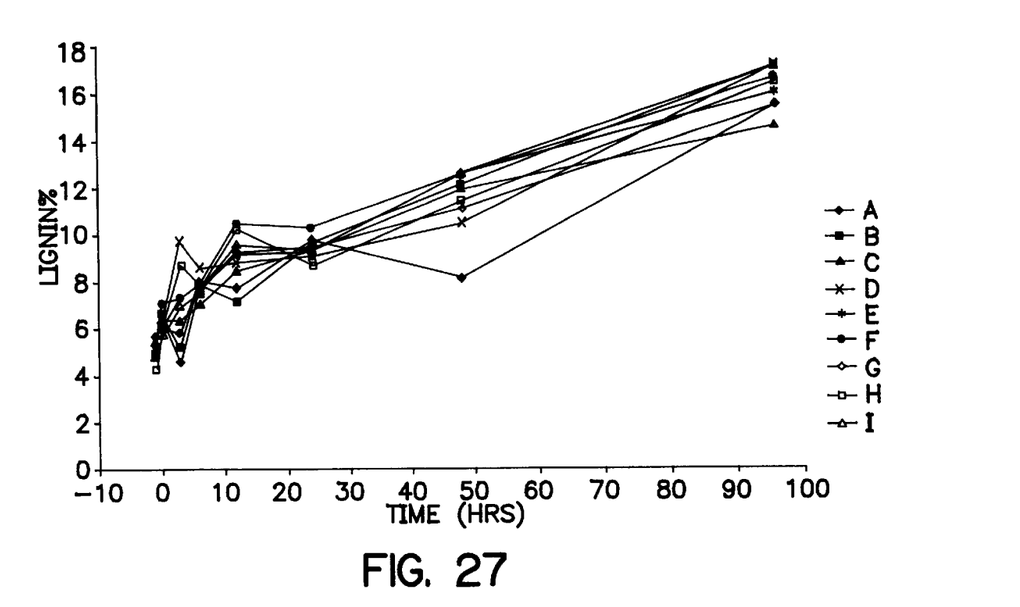
FIG. 27 is a graph showing lignin concentration versus time for the samples of FIG. 23.
Figure 28:
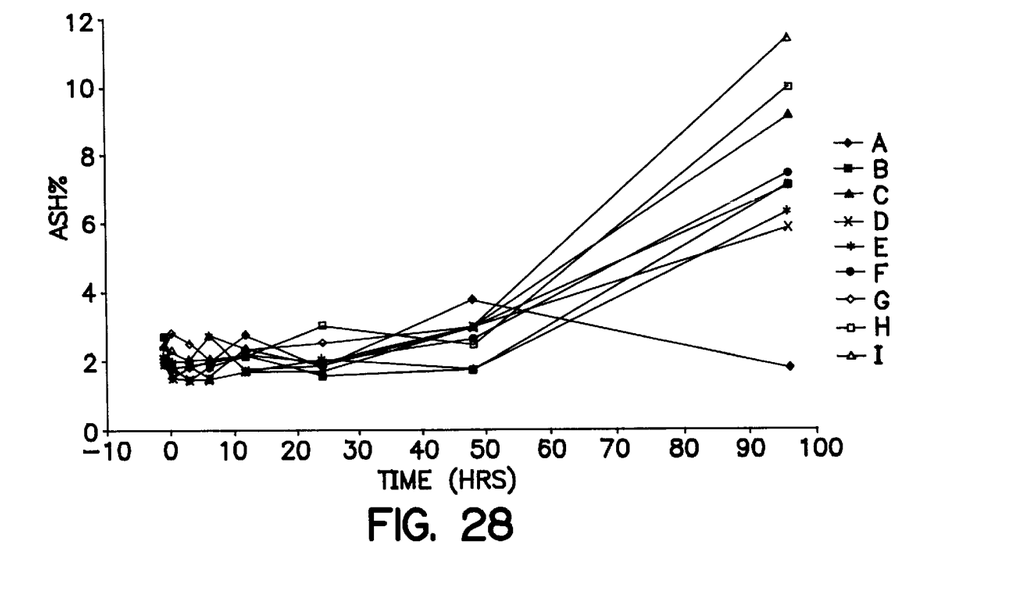
FIG. 28 is a graph showing ash content versus time for the samples of FIG. 23.
Figure 29:
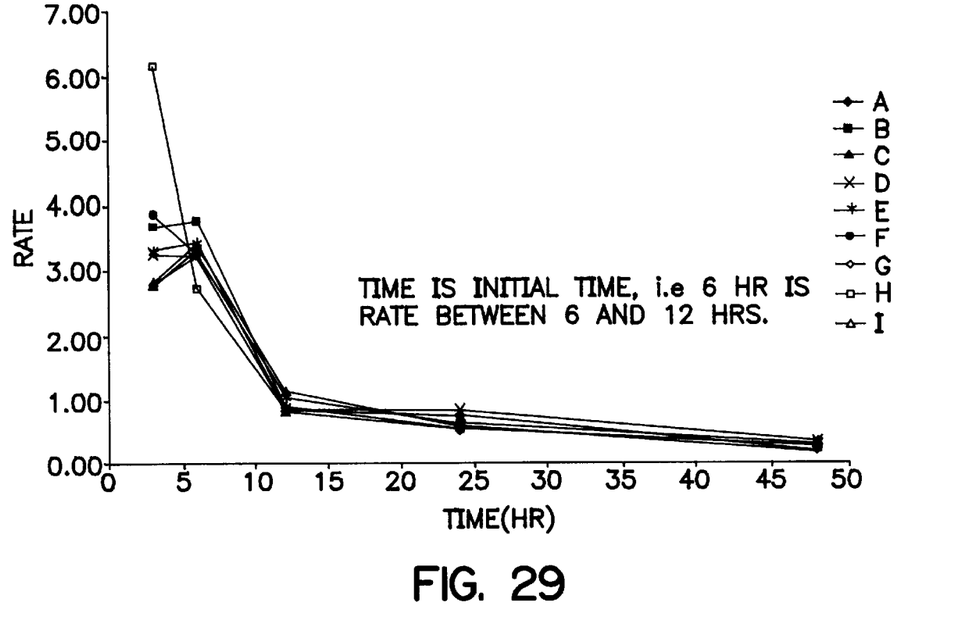
FIG. 29 is a graph showing digestion rate as a function of time for the samples of FIG. 23.

The explosions typically came at regular intervals. Some trials showed reproducibility of ±15 seconds. Depending on the ammonia load and temperature, the steady state operation was either continuous or periodic. Higher loads of ammonia (>1.5 mass ammonia/mass biomass) prompted the material to slowly discharge from the extruder apparatus 10 for several minutes and then violently discharge from the die 18A. Ammonia loads are given in a mass ratio. For example, an ammonia load of 3 signifies 3 pounds (or kilograms, or grams, etc.) of ammonia to 1 pound (or kilograms, or grams, etc.) of dry biomass. Hereafter, ammonia loads are given M/M units, connoting mass to mass ratio. Pressure was observed to build to 300 psig, and torque would approach 50%, until the explosion where pressure would drop to 0 psig and −11% torque (typical no load value). Alternatively, lower amounts of ammonia (<1.5 M/M) demonstrated continuous minor explosions which was the preferred mode of operation.

Other modifications were made as well. For example, TEFLON sheeting was used to minimize extruder pressure loss. It was observed several times that two metal-metal interfaces (the interface of the extruder apparatus 10 and die block 18, as well as between the die block 18 and the die 15A) were allowing a portion of the high pressure to escape as evidenced by slight foaming at the interface. The Teflon sheeting (not shown) was cut to fit around the orifice that it sealed and was then installed between the two surfaces. After the installation of these seals, no further foaming was observed.

The main parameters varied were temperature and ammonia loading. Water content of the biomass was also varied, but with little success. Moisture content higher than 60% led to the water being squeezed out of the biomass and flowing back to the biomass feed port. Biomass moisture levels are given as the percent of total mass (60% moisture is 60 grams of water in 100 grams of a biomass and water mixture). This created problems with feeding the biomass into the extruder apparatus 10 due to foaming in the feed tube 20 caused by the ammonia. Alternatively, moisture levels lower than 60% did not allow for effective equilibration with the ammonia, and hence, no explosions were obtained. Thus, all trials referred to in the results section were obtained at 60% moisture.

Temperature was varied in several ways at zones 1 to 3 of FIG. 11. Typically, first zone 1, centered on the biomass feed port, was unheated and cooling was shut off. In this case, heating refers to heating above room temperature. The cooling ability of the first zone was removed because it created condensation around the feed port that led to clogging of the feed. The second zone 2, at the ammonia injection point 14 was heated slightly, depending on the set point temperature of the die block 18. Too much heating would vaporize the ammonia and result in a less effective treatment. The third zone 3 was usually heated to a temperature near the average of the set points of the second zone and the die block 18 (FIG. 13). The die block 18 temperature was considered the reaction temperature. It appeared that there was an upper bound to the die block 18 temperature, as no explosions were obtained above a set point of 70° C. This is probably due in part to partial vaporization of the ammonia in the third heating zone 3. The die temperature necessarily caused a temperature rise in the third zone 3 by conductive heat transfer. This leads to an increased amount of ammonia vaporization and a less effective treatment. Additionally, the ammonia can be forced out through the biomass feed tube 20 because of a higher die block 18 temperature. Because the ammonia was not trapped as effectively as desired, the vapor was free to leave the extrusion apparatus 10. Lower temperature treatments would not generate as high a pressure towards the feed tube 20 and are not as subject to this effect.

Ammonia load was the other main parameter varied. The ammonia load was varied from 0.5 to 2.0 M/M. The calculated ammonia load is only an estimation of the actual treatment amount. The extruder apparatus 10 used had a relatively small L/D (10:1, D=30 mm), with a measured barrel 16 length of about 15.25" and the only practically allowable port 14 for ammonia injection was approximately half way down the barrel 16. This created some problems with ammonia flowing back through the biomass feed tube 20.

Several efforts were made, by altering the screw 17 configuration, to create a zone of high mixing prior to the ammonia injection port 14 that would effectively provide a plug that would restrict ammonia flow back to the feed tube 20. The screw elements 100, 101 and 102 and kneading blocks 200 and 201 are set forth in Table 2. The first three screw elements 100, 101 and 102 were permanently attached to the screw shaft due to the stresses of heating and cooling. These first sections were predominately forward transport screws which typically run at 50% capacity and did not provide an effective restriction. Thus, with a limited amount of the screw shaft available to implement the mixing zone, only five (5) mixing paddles could be used.

There were other limitations with regard to the mixing zone. Kneading blocks 200 and 201 are aligned on an individual rod 105 at various angles.

When kneading blocks 200 and 201 are aligned at angles from 0 to 90° as shown in FIGS. 6A, 6B, 6C, 6D, 6E, 6F, 6G, 6H and 6I, the forward transport of the mixing zone increases as the angle approaches 45° from either direction, and decreases as the angle diverges away from 45°. Angles are determined by looking down the rod 105 from the discharge end 15, i.e., towards the feed tube 20. The angle given is the angle of the outermost kneading block 201 to the next one 200 down the shaft 21. For example, kneading blocks 200 and 201 aligned at 30° have one paddle on the shaft, and the next one rotated 30° clockwise with respect to the previous. At 0° there is no mixing, and at 90° there is maximum mixing. Kneading blocks 200 and 201 aligned at negative angles are reversing and force the flow in the opposite direction.

The following table shows the conveyability of the kneading blocks 200 and 201 where F is forward and R is reverse.

Best ← Conveying Ability → Least
45° F   60° F   90°   60° R   45° R

Several mixing zone alignments were tried, but most of them were torque limited. In other words, only a small amount of biomass could be fed through the machine before the torque would approach its maximum value. Torque limits are dependent on rotation speed of the dual shafts 21 (supported by rods 105). Thus, a 45° mixing zone was implemented. This allowed for a good plug to be formed and also permitted a large flow of biomass. Inspection of the screw elements 100 and 101 after filling showed that the mixing zone prior to port 14 was ~90% full, while other sections beyond the port 14 were ~50% filled. Unfortunately, the length of the mixing zone was not long enough to provide a significant restriction for the ammonia vapors. So, some of the injected ammonia was lost through the feed tube 20 due to vaporization. Thus, the actual amount of ammonia used in a treatment is somewhat uncertain, but all runs were categorized by the amount of ammonia injected.

EXAMPLE 2

Initially, the primary means of quantifying the effectiveness of the process was enzymatic hydrolysis. Since the main goal was to prove the screw in barrel technology for delivering AFEX worked, maximum sugar concentrations were not the focus, but rather relative digestibility. Thus, all samples were hydrolyzed in a pH=4.8 citrate buffer with a cellulase loading of 15 IU/g and a β-glucosidase loading of 1 mL/mL of cellulase. The cellulase used was CELLUCLAST and the β-glucosidase used was NOVO 188, both by Novo Nordisk (Franklinton, N.C.). All samples were hydrolyzed at 50° C. in an agitated water bath in a 5% (weight) solution for up to 48 hours. The primary analysis took place on a lead HPLC column for glucose, xylose, galactose, arabinose and mannose. Other analyses were done on an acid column which gave glucose and composite sugar peak which consisted of xylose, mannose and galactose concentrations. Finally, a YSI (Yellow Springs, Ohio) instrument was also used and gave glucose concentrations.

Use of the die block 18 alone gave an explosion that resulted in total sugar (the sum of the concentrations of glucose, xylose, galactose, arabinose and mannose) concentration after enzymatic hydrolysis for 24 hours of 2.4 times that of completely untreated sample. The glucose concentration of this material was 2.1 times that of the completely untreated material after the same amount of time. The same material gave a total sugar concentration 2.0 times greater than the biomass treated in a screw in barrel apparatus without ammonia and the corresponding glucose concentration was 2.5 times that of the biomass treated in a screw in barrel apparatus without ammonia. Further trials with the die block 18 alone (without die 18A) gave total sugar concentrations as much as 3.5 times greater than the unprocessed material and 3.4 times greater than untreated material after 24 hours of hydrolysis.

The best results obtained with the die 18A showed a total sugar concentration 2.4 times greater than the completely untreated material after 6 hours of enzymatic hydrolysis. The glucose concentration at this point was 2.3 times greater than that obtained from completely untreated material.

In general, the most effective treatments for enzymatic hydrolysis were lower temperature runs. The higher the die block 18 temperature used (greater than 70° C.), the less effective the treatment. This may be due in part to more of the ammonia escaping the apparatus 10 at a higher temperature. However, with a lower temperature, the ammonia will remain in contact with the biomass longer and a more effective treatment is the result. The results of these tests are shown in FIGS. 19 to 22 and Table 3.

TABLE 3

Treatment Matrix for In situ Trial

| Sample | Temperature ° C. | Ammonia | Moisture |
|---|---|---|---|
| A-Untreated | 50 | N/A | 60% |
| B | No Heat | 1.0 | 60% |
| C | 55 | 1.5 | 60% |
| D | 65 | 0.8 | 60% |
| E | 65 | 1.0 | 60% |
| F | 65 | 1.5 | 60% |
| G | 65 | 1.6 | 60% |
| H | 65 | 2.0 | 60% |
| I | 55 | 1.5 | 60% |

EXAMPLE 2

After enzymatic digestibility tests, the ruminant digestibility of the material in an in-situ trial was desired. To accomplish this, several samples were generated with different temperature treatments and ammonia loads. These were taken to the Texas A & M University Animal Science Department (College Station, Tex.) and analyzed by in-situ digestibility. Samples were analyzed on a dry basis for weight loss over a known period of time. The material was placed in a small permeable bag of known weight and dried to determine the mass of dry matter. The bags were then placed in the rumen of a fistulated steer. This is a steer that has had a tube surgically inserted that allows access to the animal's rumen. By removing the bags at specific intervals (0, 3, 6, 12, 24, 48 and 96 hours), thoroughly rinsing and drying, the digestibility of the materials was determined as percent of material weight lost. The weight loss of the material in a specific bag is called the dry matter digestibility, or DMD.

An in-situ trial was run. The trial focused on screw in barrel treated materials, with the control being a sample treated at 50° C. with no ammonia.

Results of the trial are shown in FIGS. 23 to 29. The 48 hour digestibility of the trial is tabulated in Table 4. The trial showed that the digestibility of the extrusion treated material at 48 hours was up to 77.4% digestible as compared to the digestibility of 63.0% of the screw in barrel treated but untreated (by ammonia) control. Typical rumen passage time is 48 hours or less.

TABLE 4

48 Hours Dry Matter Digestibility for Trial

| ID | DMD | NH$_3$Load | T(° C.) |
|---|---|---|---|
| F | 77.4 | 1.5 | 65 |
| H | 76.1 | 2.0 | 65 |
| C | 73.5 | 1.5 | 55 |
| I | 73.4 | 1.5 | 55 |
| E | 71.6 | 1.0 | 65 |
| G | 70.5 | 1.6 | 65 |
| B | 70.4 | 1.0 | 0 |
| D | 68.0 | 0.8 | 65 |
| A | 63.0 | 0.0 | 50 |

Notes:
DMD is the dry matter digestibility, reported as a percent.
NH$_3$ Load is the mass of ammonia injected per mass of biomass treated.
T(° C.) is the Die setpoint.

At 48 hours, the effects of temperature and ammonia loading are not extremely clear. The two most effective treatments obtained are at 65° C. with an ammonia load of 1.5 and 2.0 (Samples F & H respectively). The digestibility of F (77.4%) was only slightly greater than H (76.1%). However, Sample G, with an ammonia load of 1.6 M/M and temperature 65° C. was only the 6th most digestible material, at 70.5%. The third and fourth most effective treatments (Samples C and I respectively) are duplicate samples and show excellent agreement in that they are separated by only 0.05% points and have an average digestibility of 73.5%. Samples I and C were generated at an ammonia load of 1.5 M/M with a temperature of 55° C. Throughout the trial, Samples H and F were consistently the most digestible, with sample H being the most digestible at all time points except 48 and 96 hours.

The composition of each material at each time point was determined as well. Assays were used to determine the amount of Neutral Detergent Fibers (NDF), Acid Detergent Fibers (ADF), Lignin and Insoluble Ash. The NDF assay gave the amount of cellulose, hemicellulose, lignin and ash in a sample. The ADF procedure removed the hemicellulose, the lignin procedure removed the cellulose, and the ash procedure removed the lignin.

Cellulose and hemicellulose are both considered somewhat digestible while lignin is considered indigestible. Thus, a reduction in apparent lignin content is desired, and this has been achieved. Results show that the lignin content of the samples treated in the apparatus at 65° C. were reduced up to 20.9% as compared to the control which was treated in the apparatus without ammonia, with an average of 11.9% reduction.

The rate at which digestion occurs is important as well. In all cases, the initial rate of digestion for all ammonia treated samples was higher than the material treated in the apparatus but without ammonia. In this case, the initial rate of digestion was determined as the rate of digestion between hours 3 and 6. In many cases, the samples gained weight from the 0 to 3 hour samples which does not provide acceptable data.

This may be explained by insufficient washing of the 3 hour samples which would leave dust, soluble fractions and microbes trapped in the bag. Another explanation is that the material used to fill the 0 hour bags contained more dust than the 3 hour sample, and would thus allow for more material to be rinsed out. The maximum rate of digestion was 2.25 times that of the control in the trial (untreated control). The maximum observed rate was shown by Sample H at 6.16%/hr.

The data also show that both hemicellulose and cellulose fractions decrease over time implying the digestion of these components is occurring. The hemicellulose content of the first trial decreased until 12 hours, rose at 24 hours, then decreased again until test completion. The cellulose fraction rose until 12 hours and then dropped off. This suggests that the hemicellulose is being digested first, until the cellulose is effectively broken down, then the hemicellulose is digested again. As expected, the indigestible lignin concentration steadily increased as the trial progressed.

In Examples 1 and 2, the screw in barrel apparatus 10 was used to facilitate the AFEX process. The total sugar yield from enzymatic digestibility of the corn fodder has been increased up to 250%, and the in-situ ruminate digestibility has increased 32% (from 53.8% to 71.2%) over the completely untreated sample. Additionally, the total sugar yield from enzymatic digestibility of the corn fodder has been increased up to 240%, and the in-situ ruminate digestibility has increased 19% (from 63.0% digestible to 77.4%) over the material that was treated in the screw in barrel apparatus with no ammonia. The screw in barrel process also gave results that compare well with the batch process, leading to the conclusion that such a process can be made as effective as the batch process has proven to be.

Other results of the trials are encouraging as well. A reduction in apparent lignin is desired and have been achieved with an average decrease of 11.9% (maximum reduction of 20.9% from 8.42% to 6.66%). A high rate of digestion has also been observed. The highest rates of digestion were 2.3 times the rate of digestion experienced by the control used in the respective trials. Finally, the higher level of reduction of cellulose and hemicellulose observed during the trials implies utilization of these constituents.

The system of the present invention can be used to recover the gas removed by the hood 11. Conventional gas (ammonia) receiving is used. This aspect of the present invention is well known to those skilled in the art.

Various types of equipment can be used to practice the present invention. Plastics extruders can be modified to practice the invention. Also, pulping defibrillators can be modified to perform the process of the present invention where the screw is in closely spaced contacting relation with a barrel. All of these variations will be obvious to those skilled in the art.

It is intended that the foregoing description be only illustrative of the present invention and that the present invention be limited only by the hereinafter appended claims.

We claim:

1. In a process for increasing availability of sugar content and digestibility of a lignocellulosic material by contacting the lignocellulosic material with a liquid ammonia which impregnates the lignocellulosic material and then rapidly reducing the pressure to thereby expand the lignocellulosic material by gaseous expansion of the liquid ammonia to a gas which increases availability of the sugar content and the digestibility of the lignocellulosic material, the improvement which comprises:

(a) injecting the liquid ammonia and the lignocellulosic material into a screw in a heated barrel having a feed throat leading to the screw in rotating contact with the barrel along part of a length of the screw so that the screw is sealed in operation, with an inlet for feeding the liquid ammonia into the feed throat under pressure to the screw and with heated outlet from the barrel adjacent to the screw;

(b) compacting the liquid ammonia and lignocellulosic material by rotation of the screw in the barrel;

(c) removing the liquid ammonia and the lignocellulosic material from the barrel through the outlet from the extruder so that the liquid ammonia expands explosively from the liquid to the gas in the lignocellulosic material; and (d) recovering the liquid ammonia as the gas from the lignocellulosic material.

2. The process of claim 1 wherein the barrel is at a temperature between about 30° and 100° C.

3. The process of claim 1 wherein the lignocellulosic material is corn fodder or stover.

4. The process of claim 1 wherein the lignocellulosic material has been ground to between about 0.01 and 1.0 inch and contains between about 10% to 80% by weight moisture based upon a dry weight of the lignocellulosic material before being introduced into the feed throat of the screw in barrel apparatus.

5. The process of any one of claims 1, 2, 3, or 4 wherein a die means is provided on the barrel which compresses the lignocellulosic material before removal from the screw in barrel apparatus.

6. The process of any one of claims 1, 2, 3 or 4 wherein a die block is provided on the outlet from the barrel of the screw in barrel apparatus and wherein the die block is heated to between 30° to 100° C. and wherein a die is provided on the die block which compresses the lignocellulosic material before removal from the screw in barrel apparatus.

* * * * *